United States Patent [19]

Christ et al.

[11] Patent Number: 5,750,664
[45] Date of Patent: May 12, 1998

[54] SUBSTITUTED LIPOSACCHARIDES USEFUL IN THE TREATMENT AND PREVENTION OF ENDOTOXEMIA

[75] Inventors: William J. Christ; Daniel P. Rossignol, both of Andover, Mass.; Seiichi Kobayashi, Tsuchiurashi, Japan; Tsutomu Kawata, Andover, Mass.

[73] Assignee: Eisai Co., Ltd., Tokyo, Japan

[21] Appl. No.: 461,675

[22] Filed: Jun. 5, 1995

[51] Int. Cl.$^6$ .................................................. C07H 5/00
[52] U.S. Cl. ................... 536/17.2; 536/17.1; 536/18.7; 536/55; 536/55.2
[58] Field of Search ................... 536/17.1, 17.2, 536/55.2, 53, 117, 18.7, 55

[56] References Cited

U.S. PATENT DOCUMENTS

| | | | |
|---|---|---|---|
| 4,495,346 | 1/1985 | Anderson et al. | 536/18.5 |
| 4,987,237 | 1/1991 | Myers et al. | 549/222 |
| 5,066,794 | 11/1991 | Shiba | 536/55.3 |

FOREIGN PATENT DOCUMENTS

| | | |
|---|---|---|
| 0172581A2 | 2/1986 | European Pat. Off. |
| 3135990 | 6/1991 | Japan . |
| 2179945 | 3/1987 | United Kingdom . |
| 2220211A | 1/1990 | United Kingdom . |
| WO9101134 | 2/1991 | WIPO . |

OTHER PUBLICATIONS

Bone et al., Chest: The Cardiopulmonary J. 101:1644–1655, 1992.
Knaus et al., Chest: The Cardiopulmonary J. 100:1619–1636, 1991.
Knaus et al., JAMA 269:1233–1241, 1993.
Rose et al., Infection and Immunity 63:833–839, 1995.
Ruff et al., Lymphokine: A Forum for Immunoregulatory Cell Products; Academic Press 2:235–272, 1981.
Schwartz et al., Am. J. Physiol. 267:1609–1617, 1994.
Takayama et al., Infection and Immunity 57:1336–1338, 1989.
Vogel et al., J. Immunology 124:2004–2009, 1980.
Copy of International Search Report dated Sep. 25, 1996 for PCT/US96/09578.

*Primary Examiner*—Elli Peselev
*Attorney, Agent, or Firm*—Clark & Elbing LLP

[57] ABSTRACT

Novel substituted liposaccharides useful as in the prophylactic and affirmative treatment of endotoxemia including sepsis, septicemia and various forms of septic shock and methods of using these agents are provided. Also provided are methods of preparing these agents and intermediates useful therein.

21 Claims, 3 Drawing Sheets

SUBSTITUTED LIPOSACCHARIDES USEFUL IN THE TREATMENT AND PREVENTION OF ENDOTOXEMIA

FIELD OF INVENTION

This invention relates to compounds which are useful as in the prophylactic and affirmative treatment of endotoxin exposure including sepsis, septicemia, endotoxemia and various forms of septic shock.

BACKGROUND OF THE INVENTION

The invention relates to analogs of Lipid A which are useful as inhibitors of endotoxemia.

The incidence of gram negative bacteremia in the United States has been estimated to be approximately 100,000 to 300,000 cases per year, with a mortality rate of 30–60%. Antibiotics are commonly used as the primary chemotherapy for this disease; however, their bactericidal action can result in disruption of the bacterium and concomitant release of endotoxin, i.e., the lipopolysaccharide (LPS) moiety of the bacterial outer membrane. The liberated LPS induces a number of pathophysiological events in mammals (collectively referred to as gram-negative endotoxemia or sepsis syndrome). These include fever, generalized inflammation, disseminated intravascular coagulation (DIC), hypotension, acute renal failure, acute respiratory distress syndrome (ARDS), hepatocellular destruction and cardiac failure.

Although endotoxin initiates septic shock, it has little or no direct toxic effect on tissues; instead, it triggers an immunobiological response leading to a cascade of release of cytokines such as tumor-necrosis factor (TNF), interleukin-1, interleukin-6 and interleukin-8, and other biological mediators such as nitric oxide, as well as an array of secondary mediators (e.g., prostaglandins, leukotrienes, interferons, platelet-activating factor, endorphins and colony-stimulating factors). Generation of pathophysiological concentrations of these cytokines and inflammatory mediators influence vasomotor tone, microvascular permeability and the aggregation of leukocytes and platelets causing a syndrome termed systemic inflammatory response syndrome (or SIRS) and septic shock.

The bacterial lipopolysaccharide molecule has three main regions: a long chain polysaccharide (O Antigen), a core region and a Lipid A region. The entire lipopolysaccharide molecule, as well as some of its individual components possess toxic effects described above. Most of these toxic effects, however, are believed to be attributable to the Lipid A portion. Structurally, Lipid A is composed of a disaccharide acylated by long chain fatty acids.

Therapies for endotoxin-related diseases have generally been directed towards controlling the inflammatory response. Such therapies include corticosteriod treatment, suggested to ameliorate endotoxin-mediated cell membrane injury and to reduce production of certain biological mediators; administration of antibodies designed to neutralize bacterial LPS endotoxin; treatment with naloxone which apparently blocks the hypotensive effects associate with sepsis syndrome; and treatment with nonsteroidal anti-inflammatory drugs, purported to block cyclooxygenanses and thereby decrease the production of certain secondary mediators such as prostaglandins and thromboxane.

However, none of these therapies to date has resulted in significant reduction in the morbidity and mortality resulting from sepsis and septic shock syndrome. Thus there is a long felt need for agents to affirmatively treat this disorder.

Christ, et al., "Anti-Endotoxin Compounds," U.S. Ser. No. 07/935,050, filed Aug. 25, 1992, the contents of which are included by reference, disclose certain disaccharide compounds, such as B531 shown below, useful for the treatment of endotoxemia.

Other references which disclose certain lipodisaccharides include Macher, et al., Great Britain patent 2,179, 945, Meyers, et al., Great Britain patent 2,220,211, Shiba, et al., European patent 172,581, Anderson, et al., U.S. Pat. No. 4,495,346 and Shiba, et al., U.S. Patent 5,066,794.

SUMMARY OF THE INVENTION

The present invention is directed to the treatment of sepsis, septic shock, endotoxemia and related disorders using novel lipodisaccharide analogs. The compounds of the present invention possess advantages for pharmaceutical use such as enhanced pharmacological selectivity, efficacy, and in particular increased persistence of action. A representative compound of this invention, compound 1, is shown below:

Compound 1

Further, the present invention is directed to the prophylactic and affirmative treatment of any LPS-mediated disorder. These disorders include, but are not limited to, sepsis, septicemia (including but not limited to endotoxemia), endotoxemia resulting from gram negative bacteremia (with its accompanying symptoms of fever, generalized inflammation, disseminated intravascular coagulation, hypotension, acute renal failure, acute respiratory distress syndrome, adult respiratory distress syndrome (ARDS), hepatocellular destruction and/or cardiac failure) and various forms of septic shock (including but not limited to endotoxic shock). Also, compounds of this invention will be useful in the prophylactic or affirmative treatment of localized or systemic inflammatory response to infection by different types of organisms, including gram negative bacteria, and in diseases related to translocation of gram negative bacteria or endotoxin from the gut.

Together these disorders are termed systemic inflammatory response syndrome or SIRS (For a discussion of these terms, see Bone, et al., Chest 1992; 101: 1644–55).

DEFINITIONS

In accordance with the present invention and as used herein, the following terms, are defined with the following meanings, unless explicitly stated otherwise.

The term "alkyl" refers to aliphatic organic groups which may be branched or straight and which may be optionally substituted with one or more halogen atoms at any position along the alkyl chain.

The term "prodrug" as used herein refers to any compound that has less intrinsic activity than the "drug" but when administered to a biological system generates the "drug" substance either as a result of spontaneous chemical reaction or by enzyme catalyzed or metabolic reaction. Reference is made to various prodrugs such as acyl esters, carbonates, phosphates and urethanes, included herein as examples. The groups illustrated are exemplary, not exhaustive and one skilled in the art could prepare other known varieties of prodrugs. Such prodrugs of the compounds of Formula I fall within the scope of the present invention.

The term "pharmaceutically acceptable salt" includes salts of compounds of Formula I derived from the combination of a compound of this invention and an organic or inorganic acid or base. The compounds of Formula I are useful in both non-ionized and salt form. In practice the use of salt form amounts to use of base form; both forms are within the scope of the invention.

The term "geometric isomers" refers to "trans" or "cis" (or "entgegen" or "zusammen") isomers as generally understood by those skilled in the art. All geometric isomers are within the scope of the invention.

Further, compounds of the present invention may contain asymmetric carbon atoms and hence can exist as stereoisomers, both enantiomers and diastereomers. All stereoisomers and mixtures thereof are considered to fall within the scope of the present invention. The synthetic examples cited herein provide the most preferred isomer. It is evident that in addition to the sugar moiety, additional asymmetric carbons may be present in compounds of Formula I, for example being present in the side chains. In this event, all of the resulting diastereomers are considered to fall within the scope of the present invention.

DETAILED DESCRIPTION OF THE INVENTION

NOVEL LIPOSACCHARIDES

In one aspect, the present invention relates to the novel use of substituted liposaccharides which comprise compounds of the general formula I.

where $R^1$ is selected from the group consisting of:

where each J, K and Q, independently, is straight or branched C1 to C15 alkyl; L is O, N, or C; M is O or N; and G is N, O, S, SO, or SO$_2$;

R$^2$ is straight or branched C5 to C15 alkyl;

R$^3$ is selected from the group consisting of $$\underset{A-CH=CH-B,}{\overset{O}{\|}}$$

$$\underset{\underset{B}{|}}{\overset{O}{\|}}\\A-CH=C-D,$$

$$\underset{A-C\equiv C-B,}{\overset{O}{\|}}$$

$$\underset{A-E-B-CH=CH-D, \text{ and}}{\overset{O}{\|}}$$

$$\underset{A-E-B-C\equiv C-D,}{\overset{O}{\|}}$$

where E is N, O, S, SO, or SO$_2$; each A, B and D, independently, is straight or branched C1 to C15 alkyl;

R$^4$ is selected from the group consisting of straight or branched C4 to C20 alkyl, and where each U and V, independently, is straight or branched C2 to C15 alkyl and W is hydrogen or straight or branched C1 to C5 alkyl;

R$^5$ is selected from the group consisting of: hydrogen, —J', —J'—OH, —J'—O—K', —J'—O—K'—OH, and —J'—O—PO(OH)$_2$, where each J' and K', independently, is straight or branched C1 to C5 alkyl;

R$^6$ is selected from the group consisting of hydroxy, halogen, C1 to C5 alkoxy and C1 to C5 acyloxy;

each A$^1$ and A$^2$, independently, is selected from the group consisting of

Z—CO$_2$H, and O—Z—CO$_2$H where Z is straight or branched C1 to C10 alkyl; and pharmaceutically acceptable salts thereof.

In general, preferred are compounds where:

R$^1$ is selected from the group consisting of:

where each J, K and Q independently, is straight or branched C1 to C15 alkyl;

R$^2$ is straight or branched C8 to C12 alkyl;

R$^3$ is selected from the group consisting of:

$$\underset{A-CH=CH-B}{\overset{O}{\|}} \text{ and}$$

$$\underset{\underset{B}{|}}{\overset{O}{\|}}\\A-CH=C-D$$

where each A, B and D, independently, is straight or branched C1 to C15 alkyl;

R$^4$ is where U is straight or branched C2 to C5 alkyl, V is straight or branched C4 to C10 alkyl and W is hydrogen or straight or branched C1 to C5 alkyl;

R$^5$ is selected from the group consisting of: hydrogen, —J', and —J'OH where J' is C1 to C5 straight or branched alkyl;

R$^6$ is selected from the group consisting of hydroxy, halogen, and C1 to C5 acyloxy;

each A$^1$ and A$^2$, independently, are selected from the group consisting of:

and pharmaceutically acceptable salts thereof.
Most preferred are compounds of formula 1 where:
R¹ is selected from the group consisting of:

where J is straight or branched C1 to C5 alkyl and K is straight or branched C9 to C14 alkyl;
R² is straight or branched C8 to C12 alkyl;
R³ is where A is straight or branched C6 to C12 alkyl and B is straight or branched C4 to C8 alkyl;
R⁴ is where U is straight or branched C2 to C4 alkyl, V is straight or branched C5 to C9 alkyl and W is hydrogen or straight or branched C1 to C3 alkyl;
R⁵ is C1 to C3 straight or branched alkyl;
R⁶ is hydroxy;
A¹ and A² are and pharmaceutically acceptable salts thereof.

General Synthetic Methods

This invention is also directed to processes for preparing compounds of Formula I. Disclosed herein are general synthetic routes for preparing variously substituted compounds of this invention. The synthesis for a compound of this invention, compound 1, is shown below.

Most of the reagents and starting materials are well known to those skilled in the art. Certain reagents and starting materials for this preparation are described in detail by Christ, et al., in U.S. application Ser. No. 07/935,050, the disclosure of which is hereby incorporated by reference.

One synthesis of the compounds of this invention is outlined below. Although this example describes the preparation of compound 1, use of alternate starting materials will yield other analogs of this invention. Thus the synthesis is indeed general in nature.

For example, use of alternative alkylating agents in the preparation of intermediate U will provide analogs with structurally differing substituents at R1.

The substitution pattern at R2 is controlled by the use of the proper alkylating agent in the preparation of intermediate O.

Further, substitution of suitable alternative compounds for intermediate E in the preparation of intermediate G will produce analogs which differ with respect to R3.

A representative synthesis of the R4 side chain is outlined below. The preparation of variations of this side chain may be achieved by replacing the starting material with other suitable starting materials. For example, the length or branching of this side chain may be prepared by starting with the appropriate starting material.

Thus the synthesis briefly outlined below provides versatile pathways to the compounds of this invention. (For details regarding the synthesis, see the following experimental examples.)

A representative preparation of the "left" portion is outlined below.

A representative synthesis of the "right" portion of compound 1 is shown below.

These two "halves" of the molecule are then coupled as outlined below and further elaborated to give compound 1.

-continued

T

V

W

X

Y     Z

-continued

Compound 1
(sodium salt)

FORMULATIONS

Lipid A analogs are administered in dosages which provide suitable inhibition of LPS activation of target cells; generally, these dosages are, preferably between 0.01–50 mg/patient, more preferably, between 0.05–mg/patient and most preferably, between 0.1–5 mg/patient.

The term parenteral as used herein includes subcutaneous, intravenous, intramuscular, and intraarterial injections with a variety of infusion techniques. Intraarterial and intravenous injection as used herein includes administration through catheters. Preferred for certain indications are methods of administration which allow rapid access to the tissue or organ being treated, such as intravenous injections for the treatment of endotoxemia.

Pharmaceutical compositions containing the active ingredient may be in any form suitable for the intended method of administration.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropylmethyl cellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadeaethyleneoxycetanol), a condensation product of ethylene oxide with a partial ester derived from a fatty acid and a hexitol anhydride (e.g., polyoxyethylene sorbitan mono-oleate). The aqueous suspension may also contain one or more preservative such as ethyl of n-propyl p-hydroxybenzoate.

The pharmaceutical compositions of the invention are preferably in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, such as a solution in 1,3-butanediol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

Formulations suitable for parenteral administration include aqueous and non-aqueous isotonic sterile injection solutions which may contain anti-oxidants, buffers, bacteriostats and solutes which render the formation isotonic with the blood of the intended recipient; and aqueous and non-aqueous sterile suspensions which may include suspending agents and thickening agents. The formulations may be presented in unit-dose or multi-dose sealed containers, for example, ampules and vials, and may be stored in a freeze-dried (lyophilized) condition requiring only the addition of the sterile liquid carrier, for example water for injections, immediately prior to use. Extemporaneous injection solutions and suspensions may be prepared from sterile powders of the kind previously described.

It will be understood, however, that the specific dose level for any particular patient will depend on a variety of factors including the activity of the specific compound employed; the age, body weight, general health, and sex of the individual being treated; the time and route of administration; the rate of excretion; other drugs which have previously been administered; and the severity of the particular disease undergoing therapy.

EXAMPLES

Examples of use of the method of the invention includes the following. The compounds of this invention and their preparation can be understood further by the examples which illustrate some of the processes by which these compounds are prepared or used. These examples should not be construed as specifically limiting the invention and variations of the invention, now known or later developed, are considered to fall within the scope of the present invention as hereinafter claimed.

Compounds of the present invention are referred to by compound number according to the tables below.

Formula 1

[Structure diagram showing a molecule with two sugar-like rings connected, with substituents $R_5-O$, $A^2$, $NH-R^3$, $R^6$, $A^1$, $NH-R^1$, $R^4$, $R^2$]

| Compound # | $A^1/A^2$ | $R^1$ | $R^2$ | $R^3$ |
|---|---|---|---|---|
| 1 | $OPO(OH)_2$ | $COCH_2CO(CH_2)_{10}CH_3$ | $(CH_2)_9CH_3$ | $CO(CH_2)_9CH=CH(CH_2)_5CH_3$ |
| 2 | $OPO(OH)_2$ | $COCH_2CO(CH_2)_{10}CH_3$ | $(CH_2)_9CH_3$ | $CO(CH_2)_9CH=CH(CH_2)_5CH_3$ |
| 3 | $OPO(OH)_2$ | $COCH_2CO(CH_2)_{10}CH_3$ | $(CH_2)_9CH_3$ | $CO(CH_2)_{16}CH_3$ |
| 4 | $OPO(OH)_2$ | $COCH_2CHOH(CH_2)_{10}CH_3$ | $(CH_2)_9CH_3$ | $CO(CH_2)_9CH=CH(CH_2)_5CH_3$ |
| 5 | $OPO(OH)_2$ | $COCH_2CO(CH_2)_{10}CH_3$ | $(CH_2)_9CH_3$ | $CO(CH_2)_9CH=CH(CH_2)_5CH_3$ |
| 6 | $OPO(OH)_2$ | $CO(CH_2)_9CH=CH(CH_2)_5CH_3$ | $(CH_2)_9CH_3$ | $CO(CH_2)_9CH=CH(CH_2)_5CH_3$ |
| 7 | $OPO(OH)_2$ | $CO(CH_2)_{12}CH_3$ | $(CH_2)_9CH_3$ | $CO(CH_2)_9CH=CH(CH_2)_5CH_3$ |
| 8 | $OPO(OH)_2$ | $COCH_2CH(OCH_3)(CH_2)_{10}CH_3$ | $(CH_2)_9CH_3$ | $CO(CH_2)_9CH=CH(CH_2)_5CH_3$ |
| 9 | $OPO(OH)_2$ | $COCH_2CH(OCH_3)(CH_2)_{10}CH_3$ | $(CH_2)_9CH_3$ | $CO(CH_2)_9CH=CH(CH_2)_5CH_3$ |
| 10 | $OPO(OH)_2$ | $COCH_2CH(OH)(CH_2)_{10}CH_3$ | $(CH_2)_9CH_3$ | $CO(CH_2)_9CH=CH(CH_2)_5CH_3$ |

| Compound # | $R^4$ | $R^5$ | $R^6$ |
|---|---|---|---|
| 1 | $(CH_2)_2CH(OCH_3)(CH_2)_6CH_3$ | $CH_3$ | $OH$ |
| 2 | $(CH_2)_2CH(OH)(CH_2)_6CH_3$ | $CH_3$ | $OH$ |
| 3 | $(CH_2)_2CH(OH)(CH_2)_6CH_3$ | $CH_3$ | $OH$ |
| 4 | $(CH_2)_2CH(OH)(CH_2)_6CH_3$ | $CH_3$ | $OH$ |
| 5 | $(CH_2)_9CH_3$ | $CH_3$ | $OH$ |
| 6 | $(CH_2)_2CH(OH)(CH_2)_6CH_3$ | $CH_3$ | $OH$ |
| 7 | $(CH_2)_2CH(OH)(CH_2)_6CH_3$ | $CH_3$ | $OH$ |
| 8 | $(CH_2)_2CH(OCH_3)(CH_2)_6CH_3$ | $CH_3$ | $OH$ |
| 9 | $(CH_2)_2CH(OH)(CH_2)_6CH_3$ | $CH_3$ | $OH$ |
| 10 | $(CH_2)_2CH(OCH_3)(CH_2)_6CH_3$ | $CH_3$ | $OH$ |

CHEMICAL EXAMPLES

Unless otherwise noted, all reactions were conducted under an inert atmosphere. Intermediates and final products gave spectral analysis (for example, nuclear magnetic resonance spectroscopy and/or mass spectroscopy) consistent with their proposed structures. Reactions were monitored by silica gel thin layer chromatography. Preparative chromatography, unless otherwise noted, was performed on silica gel.

Preparation of Compound 1

Example 1

Intermediate B

To a suspension of intermediate A (15 g), prepared by the method of Christ, et al., European patent application 92309057.5, in $CH_2Cl_2$ (150 mL) and 48% $HBF_4$ (29.2 g), cooled via ice-bath, was added $TMSCHN_2$ (165 mL as a 2M solution in hexane). The mixture was stirred until the reaction was almost complete by TLC and then methanol (20 mL) was added followed by acetic acid (10 mL). Aqueous sodium bicarbonate was added and the mixture extracted with methylene chloride. The mixture was dried (sodium sulfate) and the solvent removed under reduced pressure. Chromatography of the residue gave B, 14.9 g.

Example 2

Intermediate C

To a cold (0° C.) solution of B (14.9 g) in methylene chloride (100 mL) was slowly added diisobutylaluminum hydride (140 mL as a 1M solution in hexanes) until reaction was complete as determined by TLC. The reaction was quenched by the addition of aqueous 1N hydrochloric acid (100 mL) followed by conc. hydrochloric acid (50 mL). The layers were allowed to separate and the aqueous layer was re-extracted with $CH_2Cl_2$. The combined organic layers were then washed with brine, dried over sodium sulfate and concentrated under reduced pressure. After purification by silica chromatography, 12.06 g of intermediate C was obtained.

Example 3

Intermediate D

To a solution of C (10.64 g) in methylene chloride (40 mL) was added triethylamine (15.75 mL), p-toluenesulfonyl chloride (11.86 g) and dimethylaminopyridine (690 mg). The resulting suspension was allowed to stir until reaction was complete as determined by TLC then quenched via water work-up with methylene chloride extraction. After purification by silica chromatography, 18.7 g of D was obtained.

Example 4

Intermediate E

To a solution of D (18.7 g) in 200 mL of acetone was added sodium iodide (24.6 g). The mixture heated at reflux for 1½ hours, the solvent removed under reduced pressure and the residue partitioned between water and hexane. The organic layer was separated, dried (sodium sulfate) and the solvent removed. Chromatography (silica) gave 15.4 g of E as a colorless liquid.

Example 5

Intermediate F

This compound was prepared by the method of Christ, et al., European Patent Application 92309057.5.

Example 6

Intermediate G

To a solution of 18.6 g of intermediate F and 15.4 g of intermediate E in hexane was added 23.9 g of silver oxide and the mixture refluxed overnight. The mixture was cooled, filtered through diatomaceous earth, the solvent removed and the residue chromatographed (silica) to give intermediate G (21 g) as a colorless syrup.

Example 7
Intermediate H

To a cold (0° C.) solution of intermediate G (21 g) in methylene chloride was added dropwise 3.5 mL of 48% tetrafluoroboric acid. After 5 minutes, the mixture was washed with aqueous sodium bicarbonate solution and with brine. The mixture was concentrated under reduced pressure and chromatographed (silica) to give intermediate H, 18.7 g, as a colorless syrup.

Example 8
Intermediate I

To a solution of intermediate H (17.6 g) in neat methyl iodide (105 mL) was added silver oxide (83 g). The mixture was stirred overnight and then diluted with hexane and filtered through diatomaceous earth. The mixture was concentrated under reduced pressure and the residue dissolved in methylene chloride (40 mL). The mixture was cooled to 0° C. and to it was added imidazole (2.44 g) and t-butyldimethylsilyl chloride (4.7 mL). It was stirred overnight and 150 mL of sodium bicarbonate solution was added. The organic layer was dried (sodium sulfate) and chromatographed (silica) to give intermediate I, 10.5 g, as a colorless syrup.

Example 9
Intermediate J

Intermediate I was dissolved in 100 mL of methylene chloride to which as added diallyidiisopropylphosphoramidite (7.4 mL), followed by tetrazole (6.37 g). The mixture was cooled and stirred for 20 minutes. A suspension of metachloroperoxybenzoic acid (24.2 mmol) in 50 mL of methylene chloride was added over 15 minutes while the temperature of the reaction was maintained below –60° C. Sodium bicarbonate solution was added and the organic layer separated, dried (sodium sulfate) and the solvent removed under reduced pressure. Chromatography (silica) gave 14 g of a colorless syrup of intermediate J.

Example 10
Intermediate K

To a suspension of 39.5 g of di(thiophenyl)tin (prepared by the method of Christ, et al., European patent application 92309057.5) in 235 mL of methylene chloride was added thiophenol (12 mL). To this mixture was added triethylamine dropwise over 15 minutes. A portion (150 mL) of this "tin reagent" mixture was added dropwise over 15 minutes to a solution of intermediate J (12.9 g) in 25 mL of methylene chloride. The remainder of the "tin reagent" was added over 30 minutes to drive the reaction to completion. The mixture was diluted with ethyl acetate and washed with aqueous 1N sodium hydroxide and with brine. The organic layer was dried (sodium sulfate), the solvent removed and the residue chromatographed to give 11.1 g of a yellow syrup, intermediate K.

Example 11
Intermediate L

To a cold solution of intermediate K (11.1 g) and pyridine (7.1 mL) in 80 mL of methylene chloride was added trichloroethyl chloroformate (2.9 mL) and the mixture was stirred overnight. Aqueous sodium bicarbonate solution was added, the organic layer was separated, dried (sodium sulfate) and the solvent removed under reduced pressure. Chromatography gave intermediate L, 12.96 g as light yellow solid.

Example 12
Intermediate M

Intermediate L, 12.96 g, was dissolved in methylene chloride. To this mixture was added a 6M solution of hydrogen fluoride in acetonitrile and the mixture stirred for 4 hours. Aqueous sodium bicarbonate solution was added the organic layer separated, dried (sodium sulfate) and the solvent removed under reduced pressure. Chromatography gave 10.9 g of an amber syrup, intermediate M.

Example 13
Intermediate N

To a solution of intermediate M (9.5 g) in 50 mL of trichlororacetonitrile was added potassium carbonate (15 g) and the mixture stirred for 10 minutes. The mixture was filtered through diatomaceous earth and the solvent removed under reduced pressure. Chromatography gave 14.5 g, intermediate N which was used at once in Example 19.

Example 14
Intermediate O

To a solution of intermediate F (160 g) in hexane (475 mL) and iododecane (474 mL) was added silver oxide (723 g). The mixture was heated at 70° C. in the dark for 2 hours and filtered through diatomaceous earth. The solution was concentrated under reduced pressure and the residue chromatographed to give 221 g of intermediate O as a colorless oil.

Example 15
Intermediate P

To a solution of intermediate O (30 g) in methylene chloride (90 mL) and acetonitrile (90 mL)was added a solution of 48% aqueous hydrogen fluoride (9 mL) in acetonitrile (81 mL). The mixture was stirred for 30 minutes and 350 mL of aqueous sodium bicarbonate was added. The mixture was extracted with methylene chloride. The organic layer was dried (sodium sulfate), the solvent removed under reduced pressure and the residue chromatographed to yield 30 g of intermediate P as a yellow oil.

Example 16
Intermediate Q

To a cold (0° C.) solution of intermediate P (30 g) and imidazole (10.2 g) in methylene chloride (500 mL) was added t-butyldimethylsilyl chloride (10.85 g). The mixture was stirred for 1½ hours and then poured onto 400 mL of saturated aqueous ammonium chloride. The organic layer was separated, dried (sodium sulfate), the solvent removed under reduced pressure and the residue chromatographed to give 34.5 g of intermediate Q as a colorless syrup.

Example 17
Intermediate R

To a cold (0° C.) solution of intermediate Q (32.2 g) and pyridine (184. mL) in toluene (213 mL) was added a 1.94 M solution of phosgene in toluene. After 20 minutes, allyl alcohol (31 mL) was added and the mixture stirred for 30 minutes. Aqueous sodium bicarbonate was added, the organic layer separated, dried (sodium sulfate) and the solvent removed under reduced pressure. Chromatography gave 36.9 g of intermediate R as a colorless syrup.

Example 18
Intermediate S

To a solution of 2.4 mL of 48% aqueous hydrogen fluoride in 48 mL of acetonitrile was added a solution of intermediate R (20 g) in methylene chloride (24 mL) and the mixture stirred overnight. Aqueous sodium bicarbonate solution was added, the organic layer separated and dried (sodium sulfate) and the solvent removed under reduced pressure. Chromatography yielded 11 g of intermediate S as a colorless syrup.

Example 19
Intermediate T

Intermediate S (8.97 g) and intermediate N (14.5 g) were dissolved in toluene (20 mL) and the mixture dried by azeotropic removal of the solvent. This procedure was repeated three times. The dried mixture was dissolved in 50 mL of methylene chloride which was slowly added to a solution of silver triflate (5.8 g) in 50 mL of methylene chloride. The mixture was stirred for 10 minutes and 250 mL of aqueous sodium bicarbonate solution and 250 mL of 10% aqueous sodium thiosulfate was added. The organic layer was separated, dried (sodium sulfate) and the solvent removed under reduced pressure. Chromatography gave 13 g of intermediate T as a pale yellow syrup.

Example 20
Intermediate U

To a solution of intermediate T in methylene chloride (10 mL) was slowly added tin(II)tris-benzenethiolate triethylamine complex (12 mL of a 0.5M solution in methylene chloride). After 10 minutes, an additional equivalent of tin reagent was added. After an additional 15 minutes, an additional equivalent was added. After 15 minutes, ethyl acetate (250 mL) was added and the mixture extracted with 1N aqueous sodium hydroxide solution (250 mL). The mixture was dried (sodium sulfate) and concentrated under reduced pressure. Toluene was added and the solvent removed under reduced pressure to give an oil which was used in the next transformation without further purification.

Example 21
Intermediate V

To a cooled (0° C.) solution of intermediate U (2 mmol) in methylene chloride (5 mL) was added 3-ketotetradecanoic acid (997 mg), prepared by the method of Christ, et al., European patent application 92309057.5, followed by 1-(3-dimethylaminopropyl)-3-ethylcarbodiimide hydrochloride (1.5 g) and the mixture stirred for approximately 30 minutes. The mixture was diluted with methylene chloride (150 mL), washed with 1N aqueous sodium hydroxide, dried (sodium sulfate) and the solvent removed under reduced pressure. Chromatography on silica followed by chromatography on basic alumina gave 1.64 g of intermediate V.

Example 22
Intermediate W

A solution of intermediate V (1.45 g) in glacial acetic acid (5 mL) was added to a suspension of well stirred zinc copper couple (14 g) in acetic acid (10 mL). The mixture was stirred for 15 minutes and additional zinc/copper couple (10 g) was added. After an additional 15 minutes, the mixture was filtered through diatomaceous earth which was then washed with ethyl acetate. The combined washings were diluted with toluene and the solvent removed under reduced pressure. The residue was chromatographed on a bilayered mixture of basic alumina and silica to give intermediate W which was used without further purification.

Example 23
Intermediate X

A solution of intermediate W (1.02 mmol) and cis-vaccenic acid (575 mg) was dissolved in toluene (5 mL) three times and the solvent removed under reduced pressure. The dried residue was dissolved in methylene chloride (3 mL) and 1-(3-dimethylaminopropyl)-3-ethylcarbodiimide hydrochloride (780 mg) was added and the mixture stirred for 3 hours. The mixture was diluted with methylene chloride and chromatographed directly to give 734 mg of intermediate X. Further chromatography of the impure fractions gave an additional 58 mg of material.

Example 24
Intermediate Y

To a solution of intermediate X (785 mg) in methylene chloride (10 mL) was added a solution of 48% aqueous hydrogen fluoride in acetonitrile (15 mL). The mixture was stirred for 90 minutes, diluted with methylene chloride (50 mL), washed with water, and with aqueous sodium bicarbonate solution. The mixture was dried (sodium sulfate) and chromatographed to give intermediate Y, 719 mg.

Example 25
Intermediate Z

Intermediate Y (719 mg) was dissolved in methylene chloride and sodium sulfate (1.4 g) was added. Diallyidiisopropylphosphoramidite (189 μL) and tetrazole (162 mg) were added, the mixture stirred for 10 minutes and then cooled to −78° C. A solution of m-chloroperoxybenzoic acid (192 mg) in methylene chloride (4 mL) was added dropwise. The mixture was washed with aqueous sodium thiosulfate and with aqueous sodium bicarbonate, dried (sodium sulfate) and the solvent removed under reduced pressure. The residue was chromatographed to give 660 mg of intermediate Z.

Example 26
Compound 1

To a solution of tetrakis(triphenylphosphine)palladium (0) (166 mg) in 2 mL of tetrahydrofuran: acetic acid (10:1) mixture was added a solution of intermediate Z (660 mg) in 3 mL of the same solvent mixture. After 30 minutes, additional tetrakis(triphenylphosphine)palladium (0) was added. After an additional 1½ hours, toluene was added and the solvent removed under reduced pressure. The mixture was purified by chromatography on diethylaminoethylcellulose. The purified mixture was dissolved in 0.1N aqueous sodium hydroxide, filtered through a 0.45μ sterile filter and purified by HPLC on a YMC-Pack ODS-AP column to give 130 mg of compound 1.

Analytical data for some of the compounds and intermediates made by the methods described above is given below:

Compound 1: $^1$H NMR (CD$_3$OD) δ: 5.3 (1H, m), 4.6 (1, m), 4.0 (m, m), 3.9 (1H, d), 3.7 (1H, t), 3.6 (1H, t), 3.4 (3H, s), 3.3 (3H, t), 2.6 (2H, t), 2.3 (2H, m), 2.0 (2H, m), 1.7–1.2 (m, m), 0.9 (6H, t).

$^{31}$P NMR (CD$_3$OD) δ: 4.71, 3.98.

Compound 1: (M+Na)$^+$=1333
Compound 2: (M+3 Na)$^+$=1363
Compound 3: (M+3 Na)$^+$=1365
Compound 5: (M+Na)$^+$=1303
Compound 6: (M+Na)$^+$=1359
Compound 7: (M+Na)$^+$=1305
Compound 8: (M+3 Na)$^+$=1393
Compound 10: (M+Na)$^+$=1425
Intermediate G: $^1$H NMR (CDCl$_3$) δ: d, (1H), 3.9–3.7 (m, multiple), 3.65 (t,1H), 3.37 (s,3H), 3.2 (m,2H), 1.75 (q, 2H), 1.52 (s,3H), 1.4 (s,3H), 1.3 (broad m,multiple), 0.95 (s,9H), 0.9 (t,3H), and 0.2 (d,6H)

Intermediate H: $^1$H NMR (CDCl$_3$) δ:4.58 (d,1H), 4.09 (m,2H), 3.9 (dd,1H), 3.75 (dd,1H), 3.7 (m,1H), 3.5 (t,1H), 3.37 (s,3H), 3.23 (t,1H), 3.05 (t,1H), 1.8 (m, 2H), 1.68 (m,1H), 1.5 (m,1H), 1.3 (broad m,multiple), 0.95 (s,9H), 0.9 (t,3H), 0.2 (d,6H)

Intermediate I: $^1$H NMR (CDCl$_3$) δ:4.52 (d,1H), 4.05 (m,2H), 3.75 (m,1H), 3.67 (t,1H), 3.5 (t,1H), 3.45 (s,3H), 3.35 (s,3H), 3.25 (t,1H), 3.05 (t,1H), 1.8 (m,2H), 1.65 (m,1H), 1.5 (m,1H), 1.3 (broad s,m), 0.95 (s,9H), 0.9 (t,3H), 0.2 (s,6H)

Intermediate J: $^1$H NMR (CDCl$_3$) δ: 5.95 (m,2H), 5.35 (d,1H), 5.22 (d,1H), 4.6 (q,2H), 4.5 (d,1H), 4.32 (q,1H), 3.9–3.75 (m,3H), 3.7 (dd,1H), 3.65 (dd,1H), 3.45 (m,1H), 3.38 (s,3H), 3.33 (s,3H), 3.27 (t,1H), 3.2 (t,1H), 1.9–1.75 (m,3H) , 1.5 (m,1H), 1.3 (broad m,multiple), 0.95 (s,9H), 0.9 (t,3H), 0.2 (s,6H)

Intermediate L: $^1$H NMR (CDCl$_3$) δ:5.95 (d,1H), 5.4 (d,2H), 5.25 Z(d,2H), 4.95 (d,1H), 4.7 (q,2H), 4.55 (q,2H), 4.32 (q,1H), 3.9–3.75 (m,3H), 3.7 (dd,1H), 3.65 (dd,1H), 3.55 (m,1H), 3.4 (m,1 H), 3.4 (s,3H), 3.3 (s,3H), 3.25 (m,1H), 1.75 (m,multiple), 1.5–1.4 (m,2H), 1.3 (broad s,multiple), 0.95–0.9 (broad s,12H), 0.2 (d,6H)

Intermediate M: $^1$H NMR (CDCl$_3$) δ: 5.95 (m,2H), 5.75 (d,1H), 5.4 (d,1H), 5.25 (d,2H), 4.75–4.65 (dd,2H), 4.6 (q,1H), 4.3 (q,1H), 4.1 (m,2H), 3.9 (m,2H), 3.65 (m,1H), 3.4 (s,3H), 3.25 (s,3H), 1.75 (broad m,2H), 1.55–1.4 (m,2H), 1.3 (broad s,multiple), 0.9 (t,3H)

Intermediate O:$^1$H NMR (CDCl$_3$) δ:4.5 (d,1H), 3.8 (dd,1H), 3.78 (m,2H), 3.6 (m,multiple), 3.2 (m,2H), 1.5 (s,3H), 1.4 (s,3H), 1.3 (broad s, multiple), 0.95 (s,9H), 0.9 (t,3H), 0.18 (d,6H)

Intermediate P:$^1$H NMR (CDCl$_3$) δ:4.5 (d,1H), 3.75 (dd, 2H), 3.6 (q,2H), 3.5 (t, 1H), 3.3 (m,1H), 3.2 (t,1H), 3.0 (t,1H), 1.6 (m,2H), 1.25 (broad s,multiple), 0.95 (s, 9H), 0.9 (t,3H), 0.18 (d,6H)

Intermediate Q: $^1$H NMR (CDCl$_3$) δ: 4.5 (d,1H), 3.82 (t,2H), 3.7 (m,2H), 3.6 (t,1H), 3.3 (m,1H), 3.2 (t,1H), 3.05 (q,2H), 1.6 (m,2H), 1.3 (broad s,multiple), 0.95 (s,9H), 0.88 (s,9H), 0.85 (t,3H), 0.2 (d,6H), 0.1 (d,6H)

Intermediate R: $^1$H NMR (CDCl$_3$) δ:5.9 (m,1H), 5.4–5.25 (dd,2H), 4.75 (t,1H), 4.6 (d,2H), 4.45 (d,1H), 3.75 (q,1H), 3.7 (d,2H), 3.53 (q,1H), 3.38 (m,1H), 3.25 (t,1H), 3.15 (t,1H), 1.5 (t,2H), 1.25 (s, multiple), 0.95(s,9H), 0.85 (m,12H), 0.2 (s, 6H), 0.07 (s,6H)

Intermediate S:$^1$H NMR (CDCl$_3$) δ:5.9 (m,1H), 5.4–5.25 (dd,2H), 4.75 (t,1H), 4.6 (d,2H), 4.52 (d,1H), 3.7 (m,multiple), 3.65–3.6 (dd,2H), 3.55 (q,1H), 3.4 (m,1H), 3.28 (t,1H), 3.2 (t,1H), 1.5 (t,2H), 1.3 (s, multiple), 0.9 (s,9H), 0.85 (t,3H), 0.2 (s,6H)

Intermediate T: $^1$H NMR (CDCl$_3$) δ: 5.9 (m,3H), 5.6 (d,1H), 5.4–5.2 (m,6H), 4.8 (d,1H), 4.7–4.6 (m,2H), 4.55 (q,1H), 4.5 (d,1H), 4.3 q,1H), 3.8–3.7 (m,multiple), 3.6 (dd, 1H), 3.5 (m,multiple), 3.35 (s,3H), 3.2 (s,3H), 3.15 (t,1H), 1.7 (m,2H), 1.5 (m,2H), 1.3 (s,multiple), 0.95 (t,6H), 0.2 (t,6H)

Intermediate V: $^1$H NMR (CDCl$_3$) δ:7.3 (d,1H), 5.95 (m,3H), 5.6 (d,1H), 5.4–5.2 (m,6H), 4.95 (d,1H), 4.8 (d,1H), 4.7–4.5 (m,multiple)4.3 (q,1H), 3.9–3.65 (m,multiple), 3.6 (m,multiple), 3.45 (t,1H), 3.4 (t,3H), 3.35 (s,2H), 3.28 (3H), 2.5 (t,2H), 1.8 (m,2H), 1.6 (m,2H), 1.45 (m,2H), 1.3 (broad s,multiple), 0.95–0.8 (m,18H), 0.15 (d,6H)

Intermediate X: $^1$H NMR (CDCl$_3$) δ:7.3 (d,1H), 5.95 (m,4H), 5.4–5.2 (m,8H), 4.95 (d,1H), 4.8 (d,1H), 4.7 (t,1H), 4.6 (d,1H), 4.55 (q,1H), 4.3 (q,1H), 4.1 (t,1H), 3.9 (q,1H), 3.8 (t,1H), 3.7–3.5 (m,multiple), 3.45 (t,1H), 3.35 (s,3H), 3.3 (s,2H), 3.28 (s,3H), 2.5 (t,2H), 2.2 (t,1H), 2 (d,1H), 1.7 (q,2H), 1.6 (m,2H), 1.3 (s,multiple), 0.95–0.8 (m,21), 0.15 (d,6H)

Intermediate Y: $^1$H NMR (CDCl$_3$) δ: 6.65 (d,1H), 6.55 (d,1H), 5.905 (m,5H), 5.7 (m,1H), 5.4–5.2 (m,12H), 4.8 (m,2H), 4.6 (d,1H), 4.5 (m,10H), 4.3 (q,1H), 4.1 (m,1H), 3.85–3.45 (m,multiple), 3.4 (s,3H), 3.35 (s,3H), 3.25 (s,3H), 3.2 (t,1H), 2.5 (dd,2H), 2.2 (t,2H), 2 (m,mutiple), 1.7–1.2 (m,mutiple), 0.9 (t,12H).

BIOLOGICAL EXAMPLES

Both bacterial LPS and bacterial lipid A elicit production of tumor necrosis factor (TNF), IL-1β, IL-6 and IL-8 as well as other cytokines and cellular mediators in human whole blood and in a human macrophage cell lines. Generation of pathophysiological quantities of these cytokines has been found to play an important part in the initiation of the systemic inflammatory response syndrome and septic shock. The liposaccharide analogs described herein inhibit such LPS-and/or lipid A-mediated induction of cytokines as demonstrated by the following experiments.

Example A
In Vitro Inhibition of LPS-Induced Production of Cytokines

Whole human blood was prepared and tested as described (Rose et al. (1995) Infection and Immunity, 63 833–839). HL-60 cells were cultured in RPMI medium supplemented with 10% fetal calf serum and antibiotics, and induced to differentiate into macrophages by treatment with 0.1 μM 1,25-dihydroxycholecalciferol (Vitamin D3; Biomol Research Laboratories, Plymouth Meeting, Pa.), and tested for LPS mediated generation of IL-8. Briefly, bacterial LPS (i.e., from *E. coli* 0111 :B4; Sigma Chemicals, St. Louis, Mo.) at 10 ng/mL or lipid A (Daiichi Chemicals, Tokyo, Japan) were added as 10-fold concentrated solutions in $Ca^{++}$, $Mg^{++}$ free Hank's balanced salt solution (CMF-HBSS; Gibco). In experiments involving analogs of the present invention, the analog was added immediately before addition of LPS or lipid A in CMF-HBSS (e.g., between 0 and 100 μM as a 10× concentrated aliquot). Following incubation of three hours, plasma was prepared from whole blood, or culture supernatant was removed and assayed for the presence of the indicated cytokine using an ELISA assay kit from Genzyme (Cambridge, Mass.) following the instructions of the manufacturer, however, any other standard ELISA kits may be utilized. Experiments were performed in triplicate at least twice.

Figure 1:
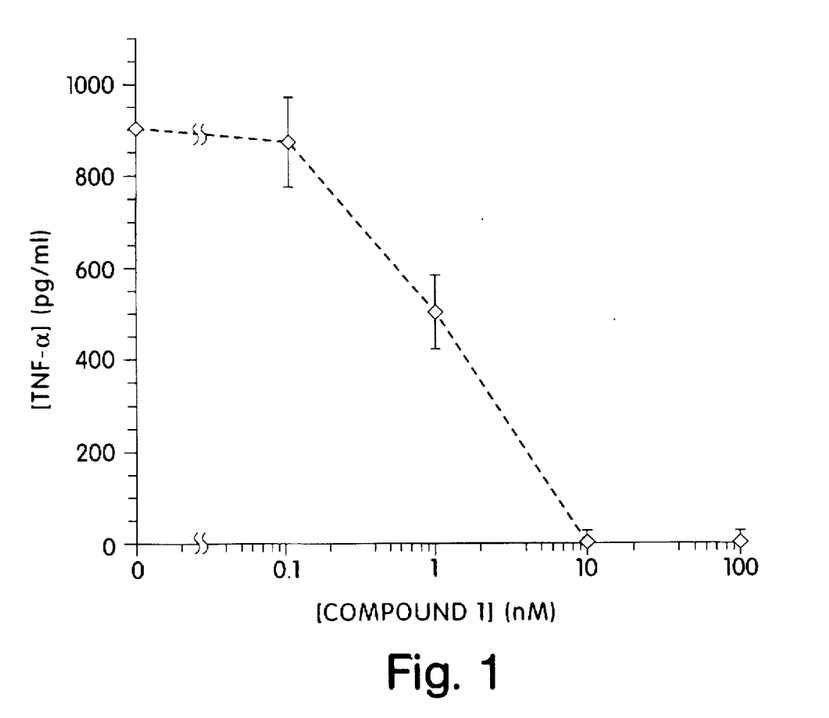
FIG. 1 depicts the inhibition of TNF-α by Compound 1 illustrating the inhibition of LPS-mediated induction of tumor necrosis factor (TNF) by a compound of this invention.

The lipid A analogs inhibited LPS-induced production of TNF in human whole blood in a concentration-dependent manner. Of the analogs tested, Compound 1 was found to be one of the most effective compounds. The results of this test are as shown in FIG. 1. Compound 1 inhibits LPS-induced production of TNF, exhibiting an $IC_{50}$ of approximately 1.5 nM. Other analogs found to inhibit LPS-induced TNF production included compound 2, compound 3, compound 4, compound 5, compound 6, compound 7, compound 8, compound 9, and compound 10. These compounds exhibited $IC_{50}$s of between 1.5 nM and 159 nM.

Compound 1 also inhibited LPS-mediated induction of IL-8 in HL-60 (human macrophage-like) cells. Inhibition of IL-8 generation was complete at concentrations of 1 nM and greater Compound 1 when either LPS or lipid A was used as agonist.

Compounds of this invention similarly inhibited the LPS-induced production of other cytokines in human whole blood, even though some of these cytokines were generated several hours after addition of LPS. For instance, IL-1β, and IL-6 requires four hours for maximum levels to be reached, while IL-8 reaches maximum levels ten hours after LPS addition. Using methods described above, compounds of this invention were added at a concentrations between 0 and 10 μM and LPS was added at 10 ng/mL. Inhibition of production of TNF, IL-1β, IL-6, and IL-8 was measured as a function of time after addition of LPS. This inhibition of cytokine generation was also found to be concentration dependent, but in all cases, suppression of all cytokine synthesis was >90% at compound 1 concentrations of 10 nM and more for up to 24 hours after addition of LPS.

Example B
Persistence of compounds in human whole blood

Figure 2:
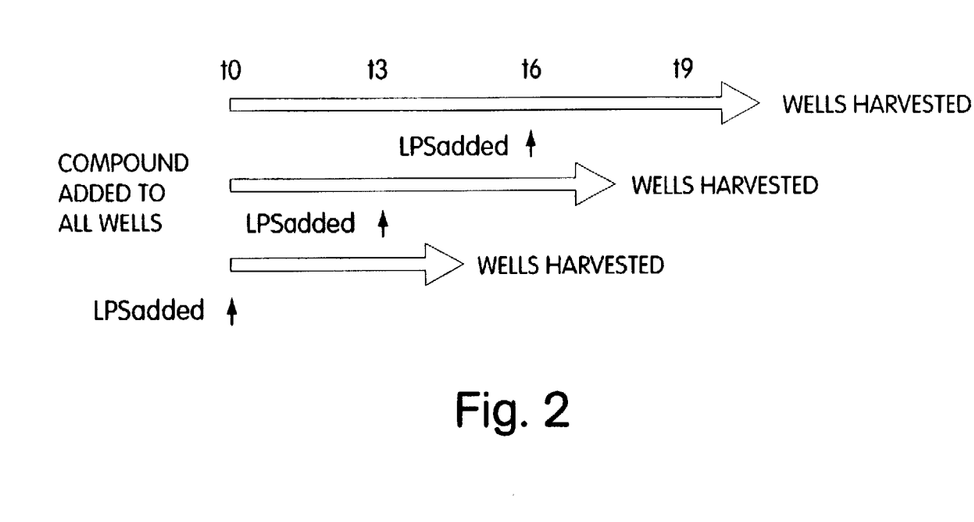
FIG. 2 depicts the general scheme used to analyze antagonistic efficacy of drug after incubation in whole blood for various times.

Although some of the compounds of this invention are not rapidly removed from the circulation, their activity diminishes with a half life of 1-3 hours. In order to maintain antagonistic efficacy, this rapid deactivation may require continuous administration. The study of this deactivation has led to the development of an assay to measure in vitro deactivation of drug in human whole blood. This is done by preincubating lipid A antagonists with blood for various periods of time followed by addition of the LPS "challenge" as described above, incubation for three hours, and assay for released cytokines. A schematic for this assay is shown in FIG. 2.

Figure 3:
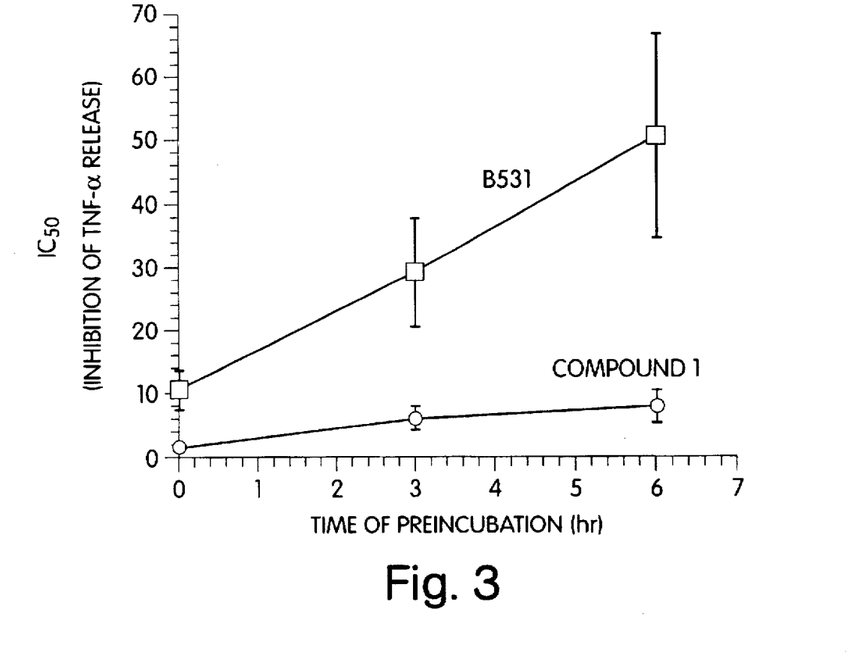
FIG. 3 depicts the relationship between time versus ability of the test compound to inhibit TNF-α and demonstrates that Compound 1 has a superior duration of action as an LPS antagonist than does B531. These data are the average of 7 separate experiments each run in triplicate.

Using this assay, it can be demonstrated that B531, as described by Christ, et al., U.S. application Ser. No. 07/935, 050, "deactivates" (loses activity with increasing time of preincubation). As shown in FIG. 3, compound 1 also deactivates, but its superior activity and decreased deactivation rate makes it as active after 6 hours as B531 was just after its addition. These data are the average of 7 separate experiments run in triplicate.

Example C
Inhibition of TNF or IL-6 Production in in vitro animal model systems LPS-induced TNF or IL-6 production was inhibited by compounds of the present invention in whole blood or macrophages isolated from guinea pigs, rats and mice. Hartley-White guinea pig (Elm Hill Breeders, Chelmsford, Mass.) and C57BL/6 mouse (Jackson Labs, Bar Harbor, Me.) macrophages were isolated from the abdomen of primed animals. Priming was accomplished by intraperitoneal injection of 2 mg of Bacillus calmette guerin(BCG; RIBI Immunochemical Research, Inc., Hamilton, Mont.) at a concentration of 10 mg/mL in physiological saline for mice and 2 mg of BCG at a concentration of 2 mg/7 mL in mineral oil for guinea pigs. Three days post-injection, peritoneal macrophages were isolated from the abdomen of the animals by standard techniques. Cells were allowed to adhere to culture plates for two to three hours and were then cultured with RPMI 1640 medium containing 10% fetal calf serum and LPS (final concentration of 10 ng/mL) was added as described above. To test inhibition, compounds of this invention (at a concentration of between 0 and 100 μM) were added to the culture medium just prior to LPS addition. Following a three-hour incubation period, guinea pig, mouse and rat TNF levels and/or IL-6 levels were assayed by ELISA, or by the cytolytic bioassay described in *Lymphokines* 2:235, 1981 for TNF released from guinea pig macrophages. In mouse peritoneal macrophages, Compound 1 provided effective inhibition ($IC_{50}$=16 nM for IL-6 and 20 nM for TNF, respectively); in guinea pig macrophages, the $IC_{50}$ for TNF release was 0.3 nM and in rat peritoneal macrophages, the $IC_{50}$ for release of TNF was 11 nM.

Example D
In Vivo Assays

BCG-primed mice (Vogel, S. et al. J. Immunology 1980, 124, 2004–2009) were utilized as an in vivo assay system for monitoring the inhibitory effects of lipid A analogs on (1) LPS-induced TNF production and (2) LPS-induced lethality as follows.

Five week old male C57BL6 mice (supra) were primed by intravenous tail vein injection with 2 mg of BCG. Ten days post-injection, *E. coli* LPS (supra) in pyrogen-free 5% glucose solution (Otsuka Pharmaceuticals Inc., Tokyo, Japan) was administered intravenously through the tail vein of the BCG-primed mice. LPS was administered at 1–3 μg/mouse for both TNF production and mortality studies. The test compound was administered as a component of the injected LPS solution at a concentration of between 3 and 300 μg/mouse. Plasma was obtained one hour post LPS injection, and TNF was assayed by the ELISA assay described above. Mortality resulting from septic shock was recorded for 36 hours after LPS injection.

Compounds of this invention effectively suppressed the production of TNF following administration of LPS. Compound 10 and Compound 1 effectively inhibited TNF production in vivo in mice ($ED_{50}$s=5 and 10.6 μg/mouse, respectively). Compound 2, compound 3, compound 4, compound 5, compound 6, compound 7, compound 8, and compound 9 also inhibited TNF production with $ED_{50}$s between 10 and 200 μg/mouse with compounds 5, 6, and 7 giving $ED_{50}$ values >100.

In parallel experiments carried out in guinea pigs, these analogs were also effective inhibitors of LPS-induced TNF production in vivo (optimum $ED_{50}$'s between 2.3 and 6.1 μg/guinea pig for compound 1, compound 7, and compound 10.

THERAPY

The lipid A analogs described herein provide useful therapeutics for the treatment or prevention of any LPS-mediated inflammation or disorder. Such disorders include without limitation: endotoxemia (or sepsis syndrome) resulting from a gram negative bacteremia (with its accompanying symptoms of fever, generalized inflammation, disseminated intravascular coagulation, hypotension, acute renal failure, acute respiratory distress syndrome, hepatocellular destruction, and/or cardiac failure); and LPS-mediated exacerbation of latent or active viral infections (e.g., infection with HIV-1, cytomegaloviruses, herpes simplex, and influenza virus).

The lipid A analog is typically administered in a pharmaceutically acceptable formulation, e.g., dissolved in physiological saline (which may include 5% glucose). When the lipid A analog is provided for the treatment of a viral infection, it may be administered in conjunction with appropriate viricidal agents. The Lipid A analog may be stored as a freeze-dried formulation.

Lipid A analogs are administered in dosages which provide suitable inhibition of LPS activation of target cells; generally, these dosages are, preferably, between 0.01–50 mg/patient, more preferably, between 0.05–25 mg/patient, and most preferably, between 0.1–5 mg/patient.

The drug should be injected or infused as soon as possible when SIRS can be diagnosed using clinical predictors such as the APACHE score (Knaus, et al., 1991 Chest 100: 1619–36 and Knaus, et al., 1993 JAMA: 1233–41) or other clinical predictors. In addition, injection or infusion should commence as soon as possible after exposure to endotoxin or diagnosis of systemic gram negative bacterial infection, especially if a more rapid or early diagnostic indicator of systematic gram negative infection becomes available.

Prophylactic indications for use of these drugs may include their use when exposure to endotoxin can be anticipated. This can occur when:

1) there is an increased probability of elevation of systemic (blood-borne) endotoxin from systemic or localized gram negative bacterial infection (such as during surgery);

2) there is an increased probability that blood levels of endotoxin may increase. In the normal physiological state, endotoxin only minimally translocates across the gut endothelium into splanchnic circulation. This translocated endotoxin is usually then cleared by the liver (and possibly other cells and organs). Increases in blood endotoxin levels can occur when the rate of endotoxin clearance by the liver (or other endotoxin sequestering cells or organs) decreases. Augmentation of gut translocation can occur after gut ischemia, hypoxia, trauma, or other injury to the integrity of the gut lining (or by drug or alcohol toxicity). Blood levels of endotoxin increase when liver function is compromised by disease (cirrhosis), damage (surgery or trauma), or temporary removal (as during liver transplantation);

3) there is an acute or chronic exposure to externally-derived endotoxin resulting in inflammatory response; this exposure can be caused by inhalation or other means of uptake of endotoxin. One example of SIRS-inducing endotoxin uptake is corn dust fever (Schwartz, et al., 1994 Am J Physiol. 267: L609–17), which affects workers in the grain industry, for example, in the American mid-west. Such workers can be prophylactically treated, e.g., daily, by inhaling an aerosolized formulation of the drug prior to beginning work in, e.g., fields or grain elevators.

For most other prophylactic and therapeutic applications, IV infusion or bolus injection will be used. Injection is most preferable, but infusion may be warranted in some cases by pharmacokinetic requirements.

The treatment should be initiated as soon as possible after diagnosis of SIRS, and should continue for at least three days, or when assessment of risk of mortality is reduced an acceptable level.

What is claimed is:

1. A compound of the formula:

where $R^1$ is selected from the group consisting of where each J, K and Q, independently, is straight or branched C1 to C15 alkyl; L is O, NH, or $CH_2$; M is O or NH; and G is NH, O, S, SO, or $SO_2$;

$R^2$ is straight or branched C5 to C15 alkyl;

$R^3$ is selected from the group consisting of where E is NH, O, S, SO, or $SO_2$; each A, B and D, independently, is straight or branched C1 to C15 alkyl;

$R^4$ is selected from the group consisting of straight or branched C4 to C 20 alkyl, and where each U and V, independently, is straight or branched C2 to C15 alkyl and W is hydrogen or straight or branched C1 to C5 alkyl;

$R^5$ is selected from the group consisting of hydrogen, J',—J'—OH, —J'—O—K',—J'—O—K'—OH, and

—J'—O—PO(OH)$_2$, where each J' and K', independently, is straight or branched C1 to C5 alkyl;

R$^6$ is selected from the group consisting of hydroxy, halogen, C1 to C5 alkoxy and C1 to C5 acyloxy;

A$^1$ and A$^2$, independently, are selected from the group consisting of

OH,

O—Z—CO$_2$H where Z is straight or branched C1 to C10 alkyl; or a pharmaceutically acceptable salt thereof.

2. A compound of claim 1 where R$^2$ is C8 to C15 straight or branched alkyl.

3. A compound of claim 1 where R$^2$ is C9 to C12 straight or branched alkyl.

4. A compound of claim 1 where R$^2$ is C10 straight or branched alkyl.

5. A compound of claim 1 where A$^1$ and A$^2$, independently, are OH or —O—PO(OH)$_2$.

6. A compound of claim 1 where R$^6$ is hydroxy.

7. A compound of claim 1 where R$^5$ is C1 to C5 straight or branched alkyl.

8. A compound of claim 1 where R$^1$ is selected from the group consisting of where each J, K and Q, independently, is straight or branched C1 to C15 alkyl.

9. A compound of claim 1 where R$^3$ is selected from the group consisting of where each A, B and D, independently, is straight or branched C1 to C15 alkyl.

10. A compound of claim 8 where the double bonds are cis or zusammen.

11. A compound of claim 8 where the double bonds are trans or entgegen.

12. A compound of claim 1 where R$^4$ is selected from the group consisting of straight or branched C4 to C20 alkyl, and where U is straight or branched C2 to C5 alkyl, V is straight or branched C5 to C12 alkyl, and W is hydrogen or straight or branched C1 to C5 alkyl.

13. A compound of claim 1 where each A$^1$ and A$^2$, independently, is selected from the group consisting of OH and —O—PO(OH)$_2$;

R$^1$ is selected from the group consisting of where each J, K and Q, independently, is straight or branched C1 to C15 alkyl;

R$^2$ is straight or branched C8 to C15 alkyl;

R$^3$ is selected from the group consisting of

A—CH=CH—B, and

A—CH=C—D,
    |
    B where each A, B and D, independently, is straight or branched C1 to C15 alkyl; R$^4$ is where U is straight or branched C2 to C5 alkyl, V is straight or branched C5 to C12 alkyl and W is hydrogen or straight or branched C1 to C5 alkyl;

and $R^5$ is straight or branched C1 to C5 alkyl; and $R^6$ is hydroxy.

14. A compound of claim 1 where $A^1$ and $A^2$ are —O—PO(OH)$_2$;

$R^1$ is selected from the group consisting of where each J and Q, independently, is straight or branched, C1 to C5 alkyl, and K is straight or branched C8 to C15 alkyl;

$R^2$ is straight or branched C8 to C15 alkyl;

$R^3$ is where A is straight or branched C5 to C12 alkyl and B is straight or branched C6 to C12 alkyl;

$R^4$ is where U is straight or branched C2 to C5 alkyl, V is straight or branched C5 to C12 alkyl and W is hydrogen or straight or branched C1 to C5 alkyl; and $R^5$ is J, where J is straight or branched C1 to C5 alkyl; and $R^6$ is hydroxy.

15. A compound of claim 1 where $A^1$ and $A^2$ are —O—PO(OH)$_2$;

$R^1$ is selected from the group consisting of where each J and Q, independently, is straight or branched is C1 to C3 alkyl, and K is straight or branched C10 to C12 alkyl;

$R^2$ is straight or branched C9 to C12 alkyl;

$R^3$ is where A is straight or branched C8 to C12 alkyl and B is straight or branched C6 to C10 alkyl;

$R^4$ is where U is straight or branched C2 to C4 alkyl, V is straight or branched C5 to C10 alkyl and W is hydrogen or straight or branched C1 to C3 alkyl; and $R^5$ is straight or branched C1 to C3 alkyl; and $R^6$ is hydroxy.

16. A compound of claim 1 where $A^1$ and $A^2$ are —O—PO(OH)$_2$;

$R^1$ is $R^2$ is (CH$_2$)$_9$CH$_3$;

$R^3$ is $R^4$ is $R^5$ is —CH$_3$; and $R^6$ is hydroxy.

17. A compound of claim 1 where $A^1$ and $A^2$ are —O—PO(OH)$_2$;

$R^1$ is $R^2$ is (CH$_2$)$_9$CH$_3$;

$R^3$ is $R^4$ is $R^5$ is —CH$_3$;

$R^6$ is hydroxy.

18. A compound of claim 1 where $A^1$ and $A^2$ are —O—PO(OH)$_2$;

$R^1$ is $R^2$ and $R^3$ are $(CH_2)_9CH_3$;

$R^4$ is $R^5$ is —$CH_3$; and $R^6$ is hydroxy.

19. A compound of claim 1 where $A^1$ and $A^2$ are —O—PO(OH)$_2$;

$R^1$ is $R^2$ is $(CH_2)_9CH_3$;

$R^3$ is $R^4$ is $R^5$ is —$CH_3$; and $R^6$ is hydroxy.

20. A compound of claim 1 where $A^1$ and $A^2$ are —O—PO(OH)$_2$;

$R^1$ is $R^2$ is $(CH_2)_9CH_3$;

$R^3$ is $R^4$ is $R^5$ is —$CH_3$; and $R^6$ is hydroxy.

21. A compound of claim 1 where $A^1$ and $A^2$ are —O—PO(OH)$_2$;

$R^1$ is $R^2$ is $(CH_2)_9CH_3$;

$R^3$ is $R^4$ is $R^5$ is —$CH_3$; and $R^6$ is hydroxy.

* * * * *